US008632502B2

(12) United States Patent
Behymer et al.

(10) Patent No.: US 8,632,502 B2
(45) Date of Patent: *Jan. 21, 2014

(54) ANCHOR DEPLOYMENT APPARATUS

(75) Inventors: Bruce A. Behymer, Grant, MN (US);
Jacob W. Silverberg, Blaine, MN (US);
Michael R. Klardie, Bloomington, MN (US);
Michael J. Kern, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 547 days.

This patent is subject to a terminal disclaimer.

(21) Appl. No.: 12/896,147

(22) Filed: Oct. 1, 2010

(65) Prior Publication Data
US 2011/0040257 A1 Feb. 17, 2011

Related U.S. Application Data

(63) Continuation-in-part of application No. 12/056,547, filed on Mar. 27, 2008, now Pat. No. 8,262,624.

(51) Int. Cl.
*A61M 5/32* (2006.01)

(52) U.S. Cl.
USPC .......................................... 604/174; 604/175

(58) Field of Classification Search
USPC .................... 604/174–179; 606/129, 151, 153
See application file for complete search history.

(56) References Cited

U.S. PATENT DOCUMENTS

| 4,122,858 | A | 10/1978 | Schiff |
| 4,230,110 | A | 10/1980 | Beroff |
| 4,278,092 | A | 7/1981 | Borsanyi |

(Continued)

FOREIGN PATENT DOCUMENTS

| DE | 10015323 | 11/2000 |
| EP | 0 865 799 | 9/1998 |
| WO | WO 03/090820 | 11/2003 |
| WO | WO 2008/088982 | 7/2008 |

OTHER PUBLICATIONS

U.S. Appl. No. 12/056,547, filed Mar. 27, 2008, Sage.
PCT Search Report and Written Opinion dated Dec. 7, 2009.

(Continued)

*Primary Examiner* — Kevin C Sirmons
*Assistant Examiner* — Imani Hayman
(74) *Attorney, Agent, or Firm* — Mueting Raasch & Gebhardt PA

(57) ABSTRACT

An anchor deployment apparatus for deploying an anchor about a therapy delivery element includes an anchor receiving element having an elongate member having a distal opening and a lumen extending proximally in the elongate member from the distal opening. The lumen of the elongate member is configured to slidably receive at least a portion of a therapy delivery element. The anchor deployment tool further includes an anchor engagement element having (i) a body forming a channel in which the elongate member of the anchor receiving element is axially movable, and (ii) an engagement feature forming at least a part of the channel. The engagement feature is configured to engage the anchor when the anchor is disposed about the elongate member and the elongate member is moved distally relative to the engagement element, and to cause the anchor to move distally along the elongate member when the feature is engaged with the anchor and the elongate member is moved distally relative to the engagement element. The anchor deployment tool also includes an alignment element secured relative to the elongate member and configured to secure the elongate member relative to the body of the anchor engagement element to restrict movement of the elongate member orthogonal to the axis of the channel. The anchor receiving element and the alignment element may be formed from the same or different parts.

20 Claims, 19 Drawing Sheets

(56) References Cited

U.S. PATENT DOCUMENTS

| | | |
|---|---|---|
| 4,632,670 A | 12/1986 | Mueller, Jr. |
| 4,676,782 A | 6/1987 | Yamamoto |
| 4,821,716 A | 4/1989 | Ghajar |
| 4,897,082 A | 1/1990 | Erskine |
| 5,053,015 A | 10/1991 | Gross |
| 5,129,891 A | 7/1992 | Young |
| 5,226,898 A | 7/1993 | Gross |
| 5,356,381 A | 10/1994 | Ensminger |
| 5,364,340 A | 11/1994 | Coll |
| 5,391,156 A | 2/1995 | Hildwein |
| 5,713,858 A | 2/1998 | Heruth |
| 5,746,722 A | 5/1998 | Pohndorf |
| 5,792,115 A | 8/1998 | Horn |
| 5,843,146 A | 12/1998 | Cross, Jr. |
| 6,395,017 B1 | 5/2002 | Dwyer |
| 6,428,557 B1 | 8/2002 | Hilaire |
| 6,447,533 B1 | 9/2002 | Adams |
| 6,554,802 B1 | 4/2003 | Pearson |
| 6,743,209 B2 | 6/2004 | Brown |
| 6,997,919 B2 | 2/2006 | Olsen |
| 7,090,661 B2 | 8/2006 | Morris |
| 7,594,911 B2 | 9/2009 | Power |
| 2003/0199853 A1 | 10/2003 | Olsen |
| 2005/0101915 A1 | 5/2005 | Morris |
| 2005/0107744 A1 | 5/2005 | Morris |
| 2006/0084940 A1 | 4/2006 | Olsen |
| 2006/0084941 A1 | 4/2006 | Olsen |
| 2006/0195066 A1 | 8/2006 | Cross, Jr. |
| 2008/0275401 A1 | 11/2008 | Sage |
| 2009/0248054 A1 | 10/2009 | Sage |

OTHER PUBLICATIONS

Partial PCT Search Report dated Sep. 2, 2009.

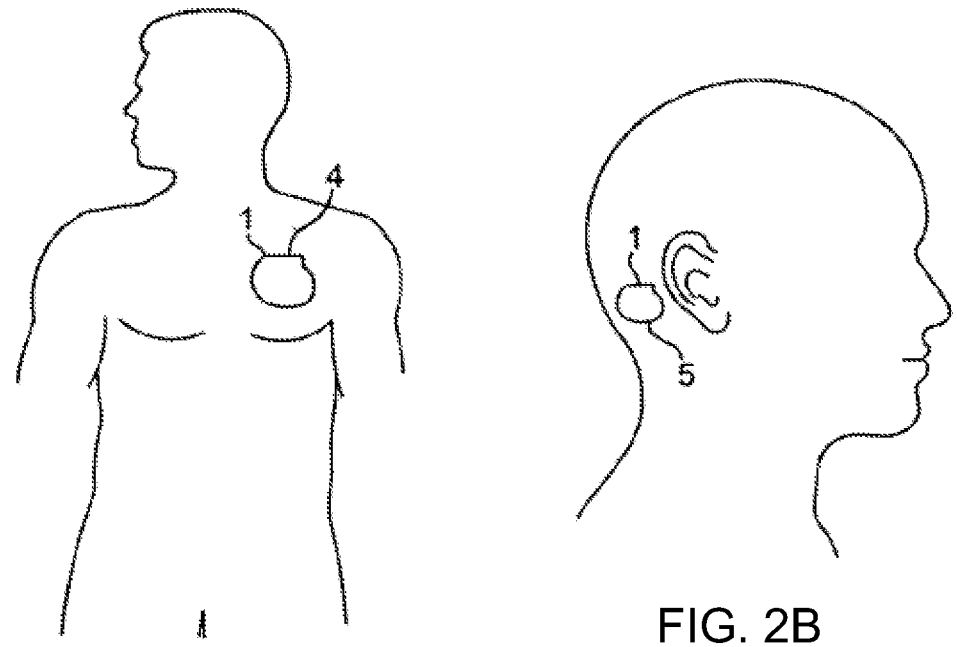
FIG. 2A
FIG. 2B
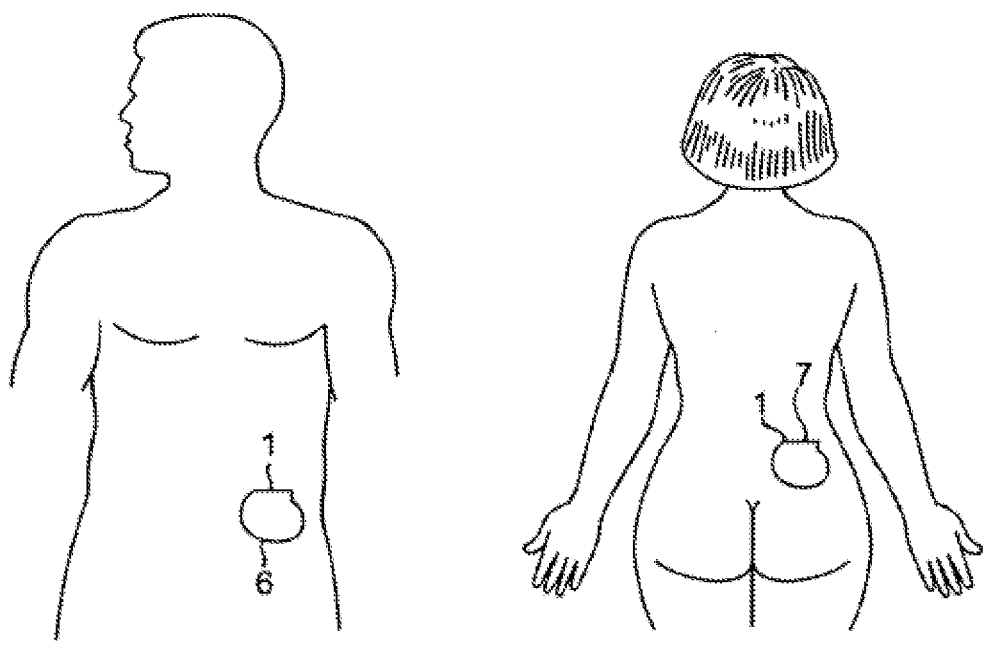
FIG. 2C
FIG. 2D

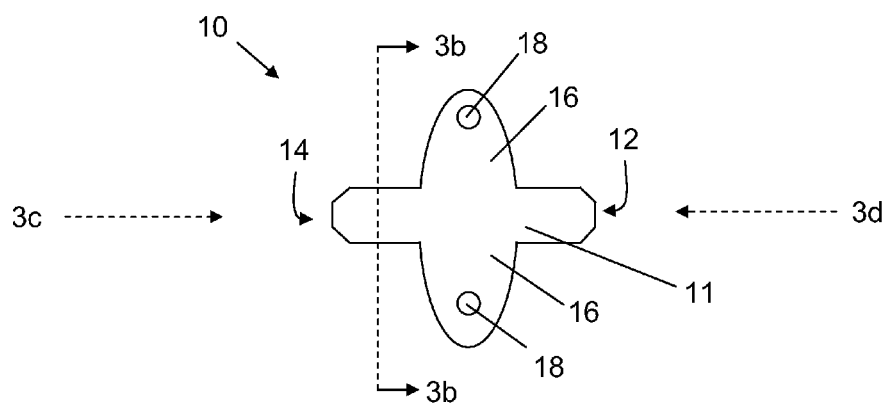
FIG. 3A
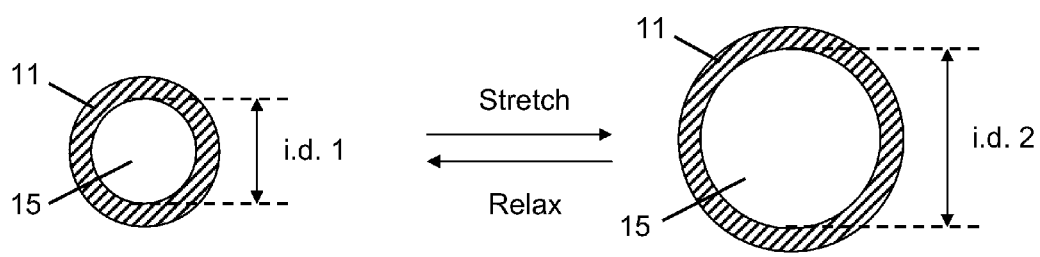
FIG. 3B
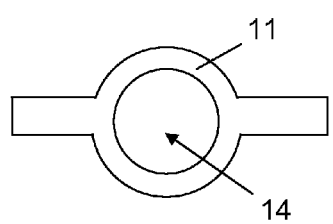 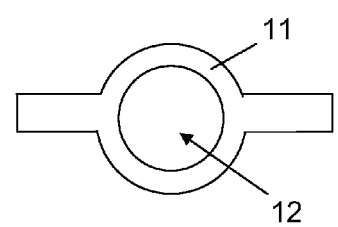
FIG. 3C　　　　　　　　　　FIG. 3D

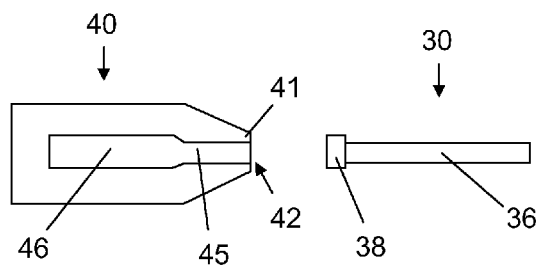
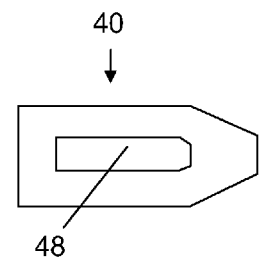
FIG. 7C                FIG. 7D
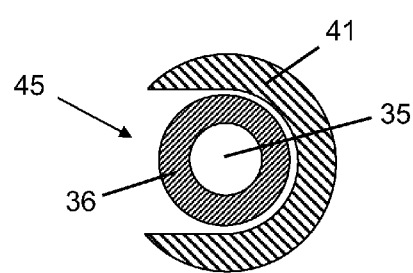
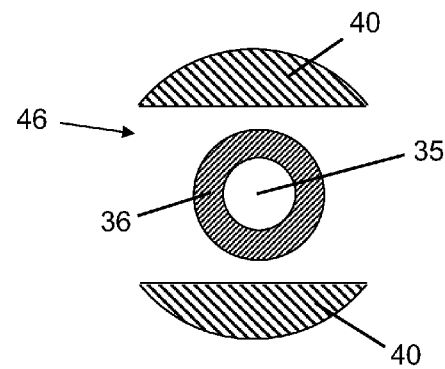
FIG. 7E                FIG. 7F
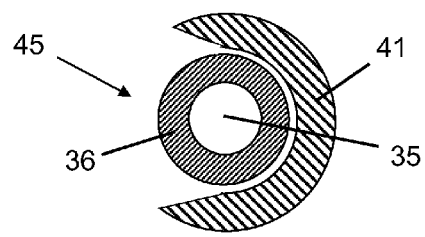
FIG. 7G

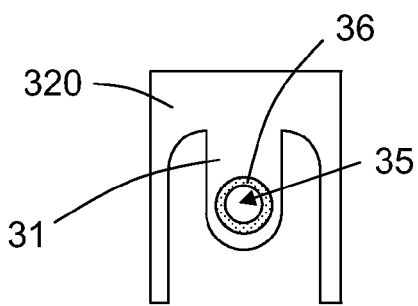 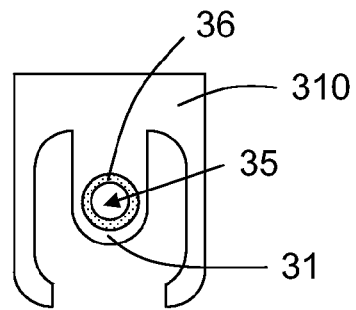
FIG. 16A  FIG. 16B
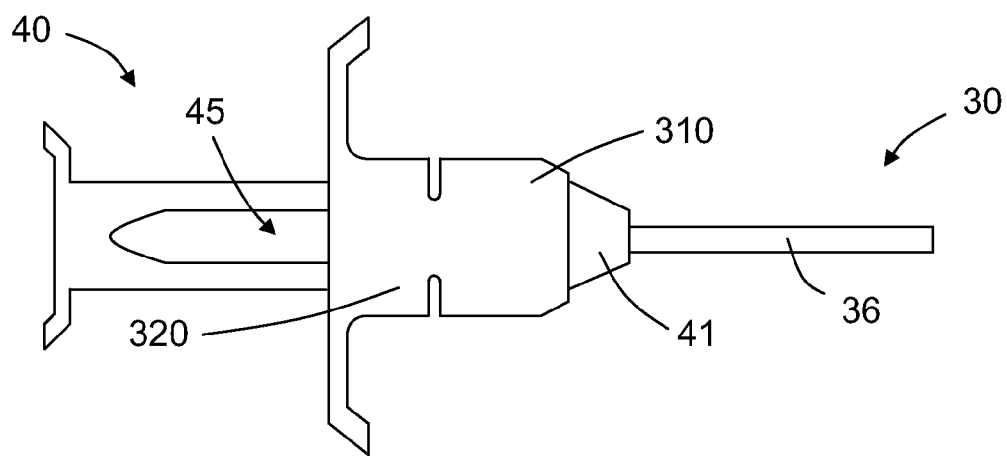
FIG. 17
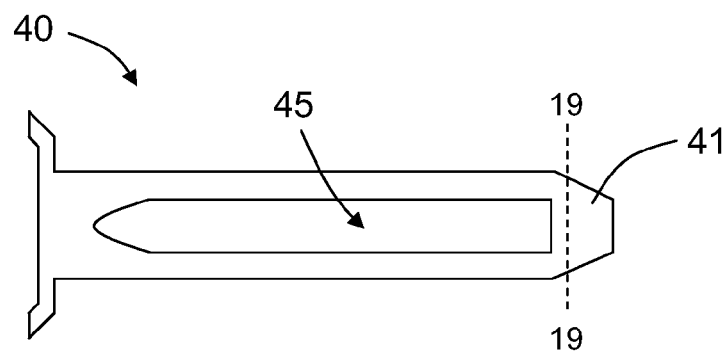
FIG. 18

ANCHOR DEPLOYMENT APPARATUS

RELATED APPLICATION

This application is a Continuation-In-Part application of U.S. patent application Ser. No. 12/056,547, filed on Mar. 27, 2008 now U.S. Pat. No. 8,262,624, and published as U.S. 2009/0248054 on Oct. 1, 2009, which is incorporated herein in its entirety to the extent that it does not conflict with the present disclosure.

FIELD

This disclosure relates, inter alia, to implantable medical devices. More particularly, it relates to anchors, anchor deployment apparatuses, and methods for retaining a therapy delivery element, such as a catheter or lead, relative to a position of a patient in which the element is implanted.

BACKGROUND

Implantable medical catheters and leads have been employed for a variety of therapeutic and diagnostic purposes. Controlled placement of such therapy delivery elements within in a patient is highly desirable, as precise placement may result in improved therapeutic efficacy or reduced side effects. However, the location of the delivery element may change in time. As the patient moves, the location of the implanted delivery element may move.

Anchors, which are typically placed about the delivery element and sutured to subcutaneous tissue of the patient, are employed to secure the position of a delivery region, e.g. infusion section or electrode, of the delivery element; e.g. catheter or lead, relative to a target location of the patient. However, existing anchors may suffer from one or more drawbacks, including (i) ineffective gripping of an implanted therapy delivery element when subjected to stresses associated patient movement, and (ii) awkward techniques for placing the anchor about the delivery element or for suturing the anchor to tissue.

SUMMARY

The present disclosure describes, among other things, anchors, anchor deployment apparatuses, kits, systems and methods that provide for effective gripping of a therapy delivery element or simple delivery of an anchor.

In an embodiment, an anchor for maintaining a portion of a therapy delivery element within a desired location of a patient is described. The therapy delivery element has an outer diameter and an outer surface about which the anchor is disposable. The anchor includes (i) a first opening, (ii) a second opening, (iii) a body member formed from elastic material disposed between the first and second opening, (iv) a lumen extending though the body member from the first opening to the second opening, and (v) a retention element secured to or integrally formed with the body member for retaining the anchor within a tissue location of a patient. The lumen is configured to be disposed about at least a portion of the outer surface of the therapy delivery element. At least a portion of the body member has a first inner diameter defined by the lumen in a relaxed state and a second inner diameter defined by the lumen in a radially stretched state. The first inner diameter is smaller than the second inner diameter. The first inner diameter is configured to be smaller than the outer diameter of the therapy delivery element, and the second inner diameter is configured to be larger than the outer diameter of the therapy delivery element.

In an embodiment, an anchor deployment apparatus for deploying an anchor about a therapy delivery element is described. The anchor deployment apparatus includes an anchor receiving element having an elongate member with a distal opening and a lumen extending proximally in the elongate member from the distal opening. The lumen of the elongate member is configured to slidably receive at least a portion of a therapy delivery element. The anchor deployment apparatus further includes an anchor engagement element having (i) a first channel in which the elongate member of the anchor receiving element is axially movable, and (ii) an engagement feature forming at least a part of the channel. The engagement feature is configured to engage the anchor when the anchor is disposed about the elongate member and the elongate member is moved distally relative to the engagement element, and to cause the anchor to move distally along the elongate member when the feature is engaged with the anchor and the elongate member is moved distally relative to the engagement element.

In an embodiment, a system is described. The system includes an anchor having a first opening, a second opening, a body member disposed between the first and second opening, and a lumen extending though the body member from the first opening to the second opening. The body member is formed from an elastic material, and at least a portion of the body member has a first inner diameter defined by the lumen in a relaxed state and a second inner diameter defined by the lumen in a radially stretched state. The first inner diameter is smaller than the second inner diameter. The system further includes a therapy delivery element having an outer diameter and an outer surface about which the anchor is disposable. The outer diameter is larger than the first inner diameter of the at least a portion of the lumen of the anchor and smaller than the second inner diameter of the at least a portion of the lumen of the anchor. The system also includes an anchor deployment apparatus including an anchor receiving element. The anchor receiving element has an elongate member with a distal opening and a lumen extending proximally in the elongate member from the distal opening. The lumen of the elongate member is configured to slidably receive at least a portion of the therapy delivery element. The elongate member has an outer diameter larger than the first inner diameter of the at least a portion of the lumen of the anchor and smaller than the second inner diameter of the at least a portion of the lumen of the anchor such that the anchor is disposable about the elongate member and, when the anchor is disposed about the elongate member, the at least a portion of the lumen of the anchor engages at least a portion of the elongate member. The anchor is moveable about the elongate member and deployable about the therapy delivery element.

In an embodiment, an anchor deployment apparatus for deploying an anchor about a therapy delivery element includes an anchor receiving element having an elongate member having a distal opening and a lumen extending proximally in the elongate member from the distal opening. The lumen of the elongate member is configured to slidably receive at least a portion of a therapy delivery element. The anchor deployment tool further includes an anchor engagement element having (i) a body forming a channel in which the elongate member of the anchor receiving element is axially movable, and (ii) an engagement feature forming at least a part of the channel. The engagement feature is configured to engage the anchor when the anchor is disposed about the elongate member and the elongate member is moved distally relative to the engagement element, and to cause the anchor to move distally along the elongate member when the feature is engaged with the anchor and the elongate member is moved distally relative to the engagement element. The anchor deployment tool also includes an alignment element secured relative to the elongate member and configured to secure the elongate member relative to the body of the anchor engagement element to restrict movement of the elongate member orthogonal to the axis of the channel. The anchor receiving element and the alignment element may be formed from the same or different parts.

By providing anchors, anchor deployment apparatuses, kits, systems and methods that provide for effective gripping of a therapy delivery element or simple delivery of an anchor, therapeutic efficacy may be enhanced or complications may be reduced.

These and other advantages will be readily understood from the following detailed descriptions when read in conjunction with the accompanying drawings.

BRIEF DESCRIPTION OF THE DRAWINGS

FIGS. 2A-D are schematic drawings of diagrammatic representations of perspective views of environments of medical devices implanted in patients.

FIG. 3A is a schematic drawing of a top view of an anchor.

FIG. 3B is a schematic drawing of a cross-section of the anchor in FIG. 3a taken through line 3b-3b.

FIGS. 3C-D are schematic drawings of head on back and front views of the anchor of FIG. 3A, as viewed along lines 3c and 3d, respectively.

FIG. 7C is a schematic drawing of an exploded side view of the anchor engagement element and anchor receiving element shown in FIG. 7A.

FIG. 7D is a schematic drawing of an opposing side view (relative to FIG. 7C) of the anchor engagement element shown in FIG. 7C.

FIG. 7E is a schematic drawing of a cross section taken along line 7e-7e of FIG. 7A.

FIG. 7F is a schematic drawing of a cross section taken along line 7f-7f of FIG. 7A.

FIG. 7G is a schematic drawing of an alternative embodiment of a cross section taken along line 7e-7e of FIG. 7A.

FIGS. 16A-B are schematic sectional views of alternative embodiments of portions of an anchor deployment apparatus with sections taken through lines 15a-15a and 15b-15b of FIG. 14, respectively.

FIG. 17 is a schematic top view of an embodiment of anchor deployment apparatus.

FIG. 18 is a schematic top view of an embodiment of a anchor engagement element of the anchor deployment apparatus depicted in FIG. 18.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein, "diameter" means a cross sectional distance from one location of a structure to a generally opposition location of the structure, and is not necessarily limited to circular cross sections. For example, a lumen may have a square, circular, oval, rectangular, or any other cross-sectional shape. Accordingly, it will be understood that "radially stretchable" means expandable such that a cross-sectional area is increasable, and is also not limited to cylindrically shaped structures.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure describes, among other things, anchors, anchor deployment apparatuses, kits, systems and methods that provide for effective gripping of a therapy delivery element or simple delivery of an anchor.

Figure 1:
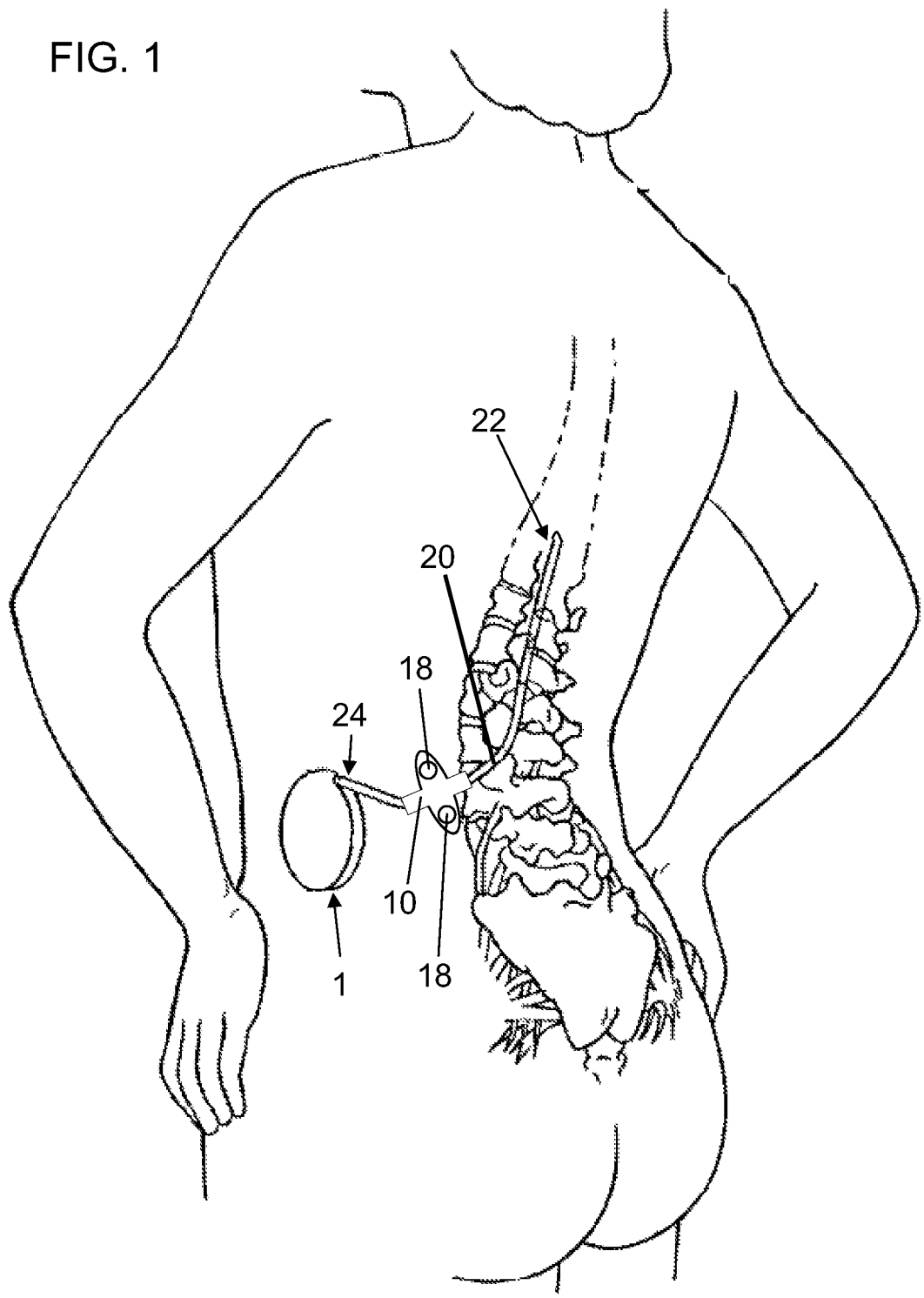
FIG. 1 is a schematic drawing of a diagrammatic representation of a perspective view of an environment of an implantable medical system in a patient.

Referring to FIG. 1, a general representative environment for an implanted medical device 1 and therapy delivery element 20 are shown. Medical device 1, such as a pacemaker, defibrillator, monitoring device, infusion device, neurostimulator, gastric stimulator, cochlar device, or the like, is subcutaneously implanted in a patient, for example in an abdominal region. A distal portion 22 of therapy delivery element 20 is positioned in the patient at a location where therapy is desired to be delivered. In the embodiment depicted, the distal portion 22 of therapy delivery element 20 is positioned within or along a spinal canal or cord of a patient. However, it will be understood that distal portion 22 of therapy delivery element 20 may be placed in any desired location to achieve its intended purpose, such as a diagnostic, monitoring, or therapeutic purpose. In the depicted embodiment, proximal end 24 of therapy delivery element 20 is operably coupled to medical device 1.

In FIG. 1, an anchor 10 is shown disposed about therapy delivery device 20. The depicted anchor 10 contains suture holes 18 for suturing the anchor 10 to tissue of the patient to maintain the position of the therapy delivery element 20 in proximity to the anchor 10 relative to a location of the patient.

Therapy delivery element 20 may be a catheter, a lead or lead extension, or the like. In numerous embodiments, therapy delivery element 20 is an elongate element that can deliver therapy, withdraw fluid, sense a parameter, or diagnose a condition. Catheters are typically flexible tubes with a lumen running from the proximal end of the catheter to one or more delivery regions that are typically located at the distal portion of catheter. A proximal end of a catheter may be coupled to an infusion medical device 1 such that fluid may be delivered from the device 1 via the lumen of the catheter to a target location of a patient via one or more delivery regions of the catheter.

Leads typically include one or more electrical contacts on a proximal end portion and one or more electrodes on a distal end portion. The contacts and electrodes are electrically coupled via insulated wires running through the lead. The contacts may be electrically coupled with an electrical signal generator medical device 1, and signals generated by the device 1 may be carried along the lead and delivered to the patient via the electrodes. A lead may be connected to a signal generator medical device 1 through a lead extension. An extension typically includes one or more contacts at the proximal and distal end portions that are electrically coupled through wires running through extension. Of course it will be understood that with some systems a lead may be directly connected to electrical signal generator medical device 1 without use of a lead extension. As used hereinafter, "leads" and "lead extensions" are used interchangeably, unless content clearly dictates otherwise.

Referring to FIG. 2, alternative locations for implanting a medical device 1 are shown. As depicted in FIG. 2A, device 1 may be implanted in the pectoral region 4 of a patient. Alternatively, device 1 may be implanted in the head 5 of a patient, more specifically behind the patient's ear (FIG. 2B), in the patient's abdomen 6 (FIG. 2C) or in the patient's lower back 7 or buttocks (FIG. 2D). Of course, device 1 may be placed in any medically acceptable location in patient.

While not shown, it will be understood that therapy delivery element 20 may be operably coupled to an external device (not shown), as opposed to or in addition to being operably couplable to an implantable device 1.

Referring now to FIG. 3, schematic drawings of various views of an embodiment of an anchor 10 are shown. As shown in the top view of FIG. 3A, anchor 10 includes a first opening 12, a second opening 14, and a body portion 11 between the first 12 and second openings 14. The body portion 11 is formed of elastomeric material. A lumen 15 (see FIG. 3B, which is a schematic of a cross section taken through line 3b-3b of the anchor depicted in FIG. 3A) extends through the body portion 11 from the first opening 12 to the second opening 14. FIGS. 3C-D are schematics of head on back and front views from the perspective of lines 3c and 3d (as shown in FIG. 3A), respectively, providing a view of first 12 and second 14 openings.

Referring to FIG. 3B, at least a portion of body 11 is radially stretchable such that the body portion 11 has a first inner diameter (i.d. 1) (defined by the lumen 15) in a relaxed state and a second larger inner diameter (i.d. 2) in a stretched state. As used herein, a "stretched state" of a body portion 11 means a state where body portion 11 has a larger inner diameter (defined by lumen 15) than in a relaxed state, and where the structural integrity of the body portion 11 is not compromised. A structurally uncompromised body portion 11 will generally be free of cracks or tears or will be capable of returning substantially to its relaxed state (i.e. to an inner diameter prior to radial stretching).

Body portion 11 of anchor 10 may be formed from any suitable elastic material. Examples of suitable elastic materials include copolymers of styrene-butadiene, polybutadiene, polymers formed from ethylene-propylene diene monomers, polychloroprene, polyisoprene, copolymers of acrylonitrile and butadiene, copolymers of isobutyldiene and isoprene, polyurethanes and the like. In various embodiments, body portion 11 of anchor 10 is formed of material capable of being stretched up to about 50% or more without substantial loss of structural integrity.

For example, body portion 11 may be capable of being stretched up to about 75% or more, 100% or more, 150% or more, or 200% or more. Silicone is an example of an elastic material that is generally expandable up to about 100% or more without substantial loss of structural integrity.

Body portion 11 may be made from the same or different material than the remainder of anchor 10. In various embodiments, the entire anchor 10 is molded from the same material.

Figure 4:
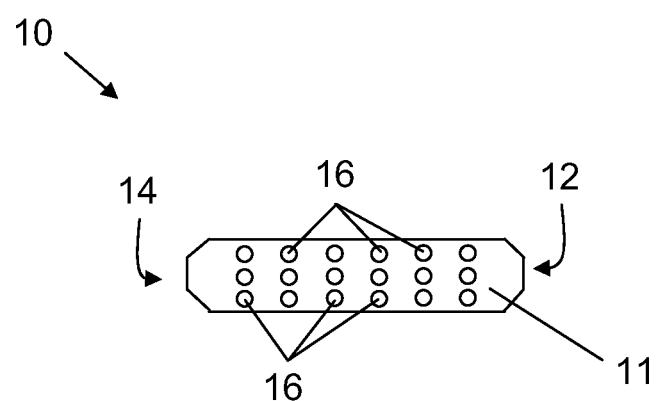
FIG. 4 is a schematic drawing of a top view of an embodiment of an anchor.

The anchor 10 depicted in FIG. 3 includes retention elements 16. One or more holes 18 may be formed in a retention element 16 for suturing anchor 10 to tissue of a patient. Retention element 16 may be coupled to or attached to (generally secured to) or may be integrally formed with body member 11. It will be understood that anchor 10 may include any number of retention elements 16. While retention elements are shown as extensions with suture holes 18, it will be understood that anchor 10 may include any suitable retention element, such as barbs, ribs, tines, or the like to retain anchor 10 with in a tissue location of a patient. For example, and with reference to FIG. 4, an anchor 10 that includes a plurality of bumps or protrusions as retention elements 16 is shown. In the embodiment depicted in FIG. 4, the protrusions 16 are arranged along a plurality of longitudinally spaced apart circumferential lines around the body 11 of the anchor 10. Of course, the protrusions may be arranged in any other suitable manner.

In various embodiments, body portion 11 of anchor 10 is free of free or substantially free of slits or openings other than first 12 and second 14 openings. In such embodiments, anchor 10, due to the elastic nature of body member 11, may provide a uniform radially compressive force against a therapy delivery element about which the anchor 10 is disposed. The absence of slits or other openings may allow for improved gripping by anchor 10 of a therapy delivery element. It will be understood that, in various embodiments, slits or other openings in body member 11 may be present, provided that anchor 10 is capable of grippingly engaging a therapy delivery element with a desired retention force.

Referring now to FIG. 5, schematic drawings of various views of an embodiment of a system including an anchor 10, therapy delivery element 20, and an anchor receiving element 30 are shown. The anchor receiving apparatus 30, as depicted, may serve as an anchor deployment apparatus. FIG. 5A depicts a schematic of a top view of a representative system; FIG. 5B is a schematic of a cross section taken through line 5b-5b of FIG. 5A; FIG. 5C is a schematic of an exploded top view of the system depicted in FIG. 5A; and FIGS. 5D-E are schematics of head on front and back views of anchor receiving apparatus 30 taken along lines 5d and 5e, respectively, of FIG. 5C. The anchor receiving apparatus 30 includes an elongate member 36 and a distal opening 32. Elongate member forms a cavity or lumen 35 in communication with distal opening 32. Lumen 35 is configured to slidably receive proximal portion 24 of therapy delivery element 20. In numerous embodiments, anchor receiving element 30 includes a proximal opening 34 and lumen 35 extends within elongate member 36 from the distal opening 32 to the proximal opening 34. In such configurations, therapy delivery element 20 may be slid through lumen 35 of anchor receiving element 30 such that proximal end 24 of therapy delivery apparatus 20 may extend beyond proximal opening 34 of anchor receiving element 30 (not shown in FIG. 5).

Figure 5A:
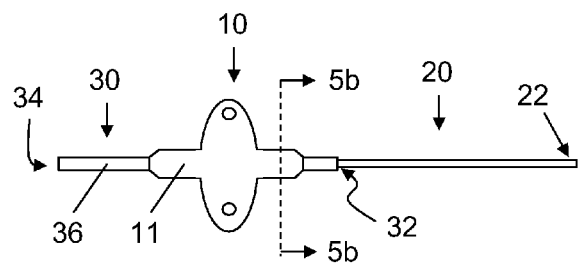
FIG. 5A is a schematic drawing of a top view of a representative system including an anchor, anchor receiving element, and a therapy delivery element.
Figure 5B:
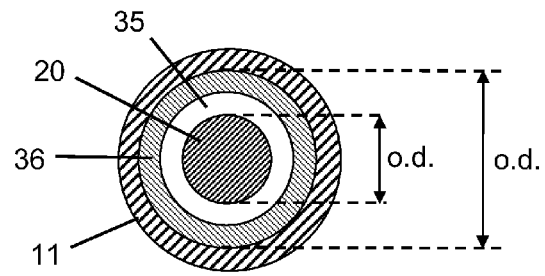
FIG. 5B is a schematic drawing of a cross section taken through line 5b-5b of FIG. 5A.
Figure 5C:
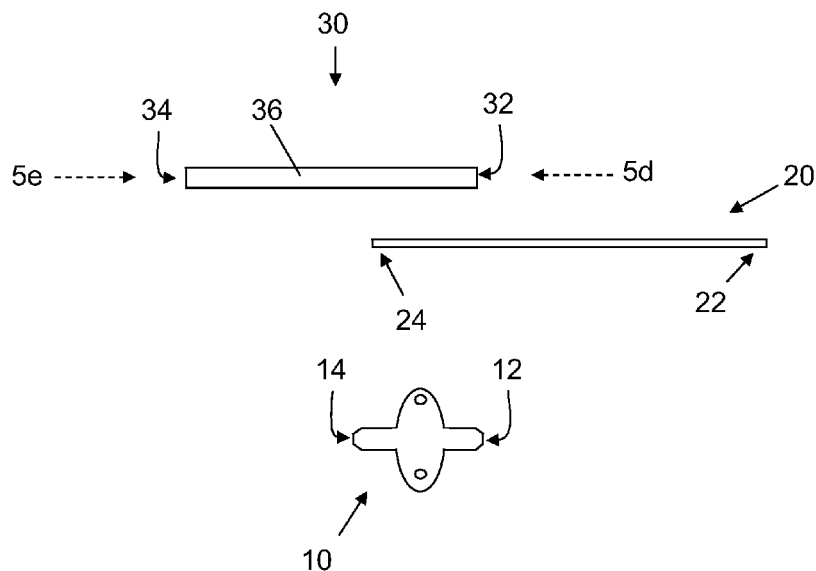
FIG. 5C is a schematic drawing of an exploded top view of the system of FIG. 5A.
Figure 5D:
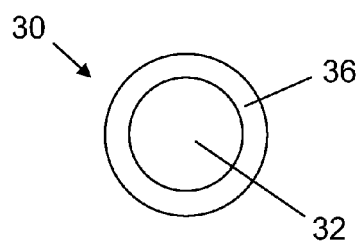
FIGS. 5D-E are a schematic drawings of head on front and back views of the anchor receiving element depicted in FIG. 5C as viewed along lines 5d and 5e, respectively.
Figure 5E:
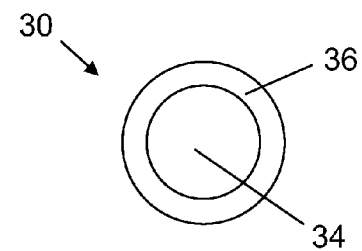

As depicted in FIGS. 5A-B, anchor 10 is disposed about anchor receiving element 30. Body member 11 of anchor 10 is disposed about and snuggly engages an outer surface of elongate member 36 of anchor receiving apparatus 30. Elongate member 36 of anchor receiving apparatus 30 has an outer diameter (o.d.) that is larger than the relaxed inner diameter (i.d. 1, see FIG. 3B) defined by lumen 15 of anchor 10 and that is smaller than a stretched inner diameter (i.d. 2, see FIG. 3B) defined by lumen 15 of anchor 10. As such, elastic body portion 11 of anchor 10 may be radially stretched so that body portion 11 anchor 10 can be positioned about elongate member 36 of anchor receiving element 30. The elastic properties of the material forming body member 11 of anchor 10 allow body member 11 to snuggly engage the outer surface of elongate member 36 of the anchor receiving element 30.

With reference to FIG. 5B, elongate body member 36 of anchor receiving apparatus 30 defines a lumen 35. The lumen 35 is configured to slidably receive at least a portion of therapy delivery element 20. Therapy delivery element 20 has an outer diameter (o.d.) that is larger than the relaxed inner diameter (i.d. 1, see FIG. 3B) defined by lumen 15 of anchor 10 and that is smaller than a stretched inner diameter (i.d. 2, see FIG. 3B) defined by lumen 15 of anchor 10. It will be understood that therapy delivery element 20 is depicted in FIG. 5B as solid for purposes of illustration. If therapy delivery element 20 were a catheter, a lumen might be depicted; if therapy delivery element 20 were a lead, an insulated conductor might be depicted; etc.

Figure 6A:
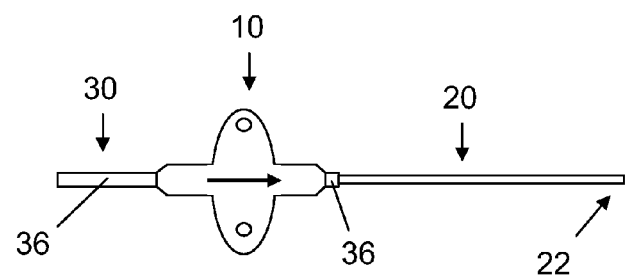
FIGS. 6A-B are schematic drawings of a representative system showing deployment of an anchor from about an anchor receiving element to about a therapy delivery element.
Figure 6B:
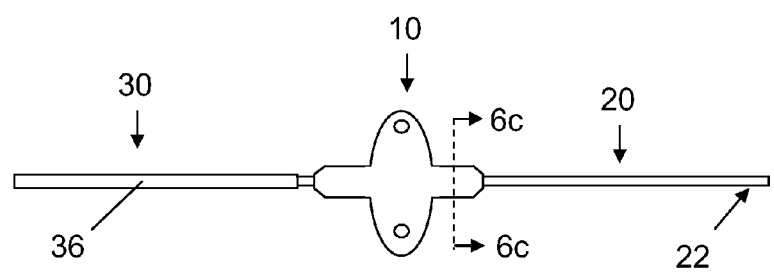

Referring now to FIG. 6A, which is the same top view of the system shown in FIG. 5A, except that anchor 10 is depicted as being moved distally (in direction of arrow) along elongate body member 36 of anchor receiving apparatus 30. Anchor 10 is slidably moveable off distal end of elongate member 36 onto therapy delivery device 20, the proximal portion 24 of which is disposed within lumen 35 of anchor receiving element 30 (see, e.g., FIG. 5).

Figure 6C:
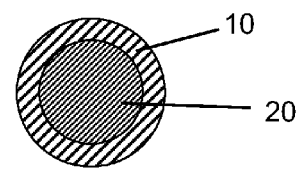
FIG. 6C is a schematic drawing of a cross section of an anchor disposed about a therapy delivery element taken along line 6c-6c of FIG. 6B.

Anchor 10 may be moved distally about elongate member 36 and onto therapy delivery element 20 through any acceptable manner, including by pushing or pulling. For example, anchor 10 may be manually moved by a physician's fingers in some embodiments. In some embodiments, anchor 10 is pushed with an anchor engagement element; e.g., as discussed below with regard to FIGS. 7-19. When body member 11 of anchor 10 is disposed about therapy delivery element 20, body member snuggly engages at least a portion of the outer surface of therapy delivery element 20 (see e.g., FIG. 6C), due to elastic properties of body member 11 and the larger outer diameter of therapy delivery element 20 relative to the relaxed inner diameter of body member 11 defined by lumen 15.

Preferably, anchor body member 11 grips therapy delivery element 20 with sufficient force to prevent movement of anchor 10 relative to therapy delivery element 20 under typical forces experienced when anchor 10 is disposed about a therapy delivery element 20 and is suture to a patient. In various embodiments, a pull force of about 1 lbf (0.45 kilogram-force) or more is required to longitudinally move anchor 10 relative to a therapy delivery element 20 that the anchor 10 is disposed about. For example, a pull force of about 2 pound-force (0.9 kilogram-force), about 3 pound-force (1.4 kilogram-force), about 4 pound force (1.8 kilogram-force), about 5 pound-force (2.3 kilogram-force), about 6 pound-pound force (kilogram-force), or more may be required to longitudinally move anchor 10 relative to a therapy delivery element 20. It will be understood that, in addition to the elastic properties of anchor body member 11, other material properties of anchor body 11 and therapy delivery element 20 may affect the pull force required to move anchor 10 along therapy delivery element 20. For example, friction due to various interactions may play a significant role.

In many embodiments, the pull force required to move anchor 10 about elongate member 36 of anchor receiving element 30 is less than the pull force required to move anchor 10 about therapy delivery element 20. This can be accomplished, despite a larger outer diameter of elongate member 36 (relative to therapy delivery element 20) by forming elongate member 36 from material that decreases frictional interaction between anchor 10 and elongate member 36. For example, elongate member 36 may be formed of higher durometer material than therapy delivery element 20. By way of another example, elongate member 36 may be coated with a material to reduce friction, such ethylene tetrafluoroethylene (ETFE) or polytetrafluoroethylene (PTFE).

Elongate member 36 of anchor receiving element 30 may be made of any suitable material. Preferably, elongate member 36 is formed from a rigid material, such as stainless steel, titanium, polycarbonate, polypropylene, or the like.

If anchor 10 is to be sutured to tissue of a patient, it may be desirable to suture anchor 10 while it is disposed about elongate member 36 of anchor receiving element 30 to prevent potential damage to therapy delivery element 20 due to accidental piercing of therapy delivery element 20 with a suture needle. Further, anchor receiving element 30, due to the rigidity of elongate member 36, allows for an implanting physician to maintain the location of anchor 10 with one hand and to suture anchor 10 with the other hand. If anchor 10 is sutured to tissue while disposed about anchor receiving element 30, at least the proximal portion 24 of the therapy delivery element 20 will preferably be disposed within lumen 35 of elongate member 36 to allow transfer of anchor 10 from anchor receiving element 30 to therapy delivery element 20.

Figure 7A:
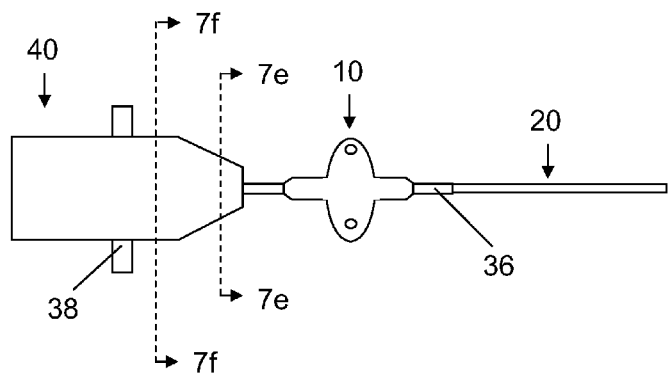
FIG. 7A is a schematic drawing of a top view of a system including an anchor, a therapy delivery element, and an anchor deployment apparatus that includes an anchor receiving element and an anchor engagement element.
Figure 7B:
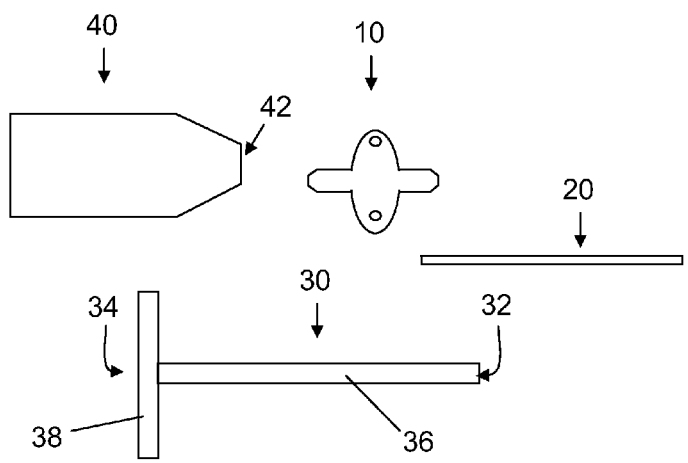
FIG. 7B is a schematic drawing of an exploded top view of the system depicted in FIG. 7A.

Referring now to FIG. 7, schematic drawings of various views of an embodiment of a system are shown. The system includes an anchor engagement element 40 and an anchor receiving element 30, collectively referred to as an anchor deployment apparatus, an anchor 10 and a therapy delivery element 20. FIG. 7A is a top view of the system; FIG. 7B is an exploded top view of the system depicted in FIG. 7A; FIG. 7C is an exploded side view of an embodiment of an anchor engagement element 40 and anchor receiving element 30 depicted in FIG. 7A; FIG. 7D is an opposing side view (relative to FIG. 7C) of anchor engagement element 40; FIG. 7E is a cross section taken along line 7e-7e of FIG. 7A, FIG. 7F is a cross section taken along line 7f-7f of FIG. 7A; and FIG. 7G is a an alternative embodiment (relative to FIG. 7E) of a cross section taken along line 7e-7e of FIG. 7A. In the embodiment depicted in FIGS. 7A-C, anchor receiving element 30 includes a handle 38 at proximal end of elongate member 36. Handle 38 is positioned generally perpendicular to the longitudinal axis of elongate member 36. The anchor receiving element 30 including handle 38 may contain a proximal opening 34 such that lumen 35 extends within elongate member 36 from proximal opening 34 to distal opening 32. Handle 38 may be made from the same or different material than elongate body 36.

Referring to FIGS. 7C-F, anchor engagement element 40 has a proximal opening 42. In proximity to or adjacent to the opening 42, the engagement element 40 contains an anchor engagement feature 41. The proximal opening 42 is in communication with a channel 45 formed within the body of the element 40. The channel 45 runs generally longitudinally within at least a proximal portion of engagement element 40. Channel 45 is configured such that at least a distal portion of elongate member 36 of anchor receiving element 30 may be slidably disposed within channel 45. In the depicted embodiment, a larger second channel 46 is formed within engagement element 40. The second channel 46 is in communication with and an extension of the first channel 45. On a side of engagement element 40 generally opposing the opening of the second channel 46, a slot 48 is formed within the body of the element 40. The slot 48 and the second channel 46 form an uninterrupted passageway through the engagement element 40. The passageway formed by the slot 48 and second channel 46 is configured such that handle 38 of anchor receiving element 30 is slidably disposable within the passageway. When anchor receiving element 30 is slidably disposed with anchor engagement element 40, a portion of either side of handle 38 of receiving element 30 extends beyond the body of engagement element 40.

Referring to the alternative embodiments depicted in FIG. 7G, channel 45 may be tapered inwardly to facilitate insertion of elongate member 36 of receiving element 30 into channel 45. In the embodiments depicted in FIGS. 7C, 7E and 7G, engagement feature 41 defines channel 45 and defines opening 42. The radial dimensions of the channel 45 may be larger or substantially the same as the outer diameter of the elongate member 36.

Figure 8A:
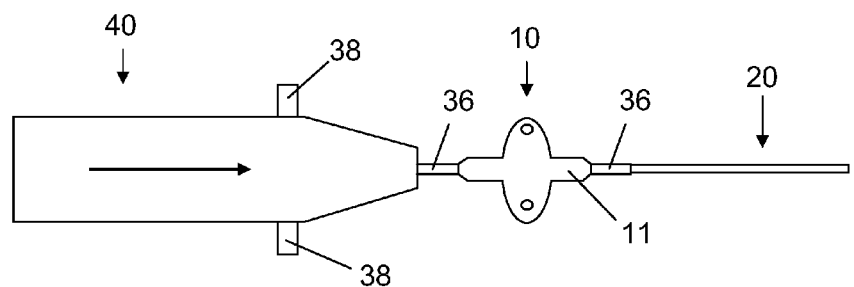
FIGS. 8A-C are schematic diagrams of top views of a system showing an anchor engagement element employed to move an anchor along an anchor receiving element and onto and about a therapy delivery element.
Figure 8B:
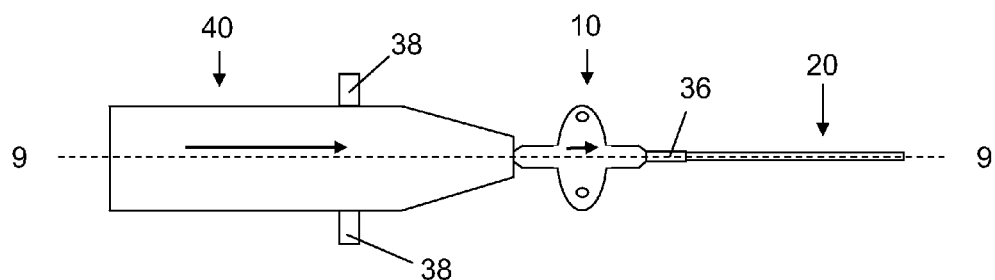
Figure 8C:
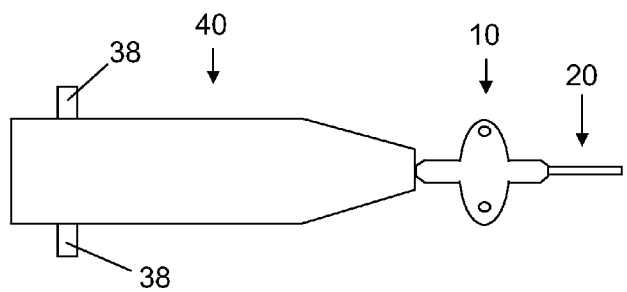

Referring to FIG. 8, anchor engagement element 40 may be moved distally relative to anchor receiving element 30 (see FIG. 8A) such that engagement element 40 may force an anchor 10 disposed about elongate body 36 of receiving element 30 to move distally along the elongate body 36 (see FIG. 8B). Continued movement of engagement element 40 distally relative to anchor receiving element 30 results in anchor 10 being transferred about therapy delivery element 20 (see FIG. 8C). Anchor engagement element 40 may be moved distally relative to anchor receiving element 30 by pushing engagement element 40 relative to receiving element 30 or by pulling protruding portions of handle 38 relative to engagement element 40.

Figure 9:
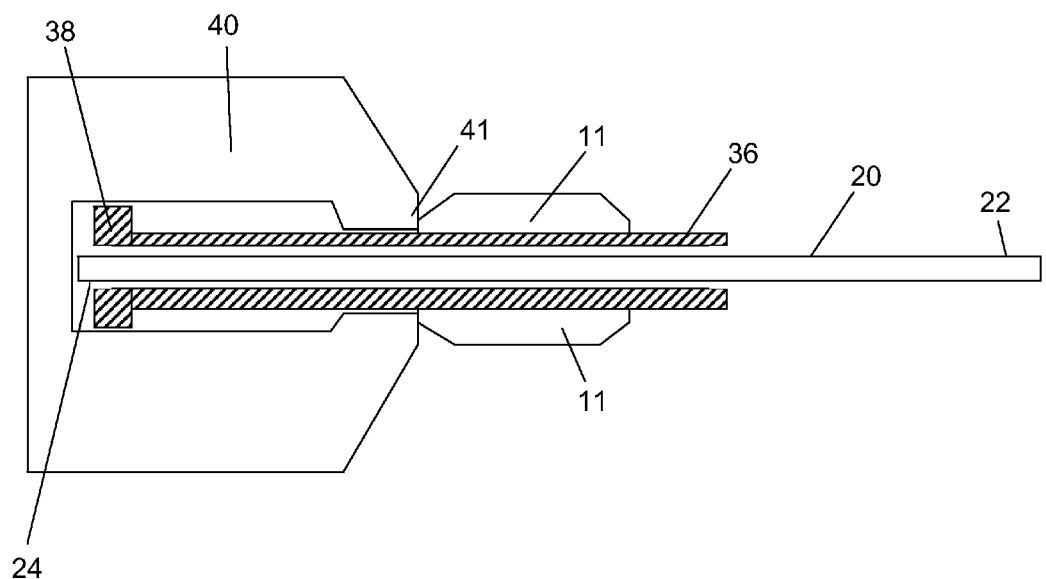
FIG. 9 is a schematic drawing of a side view of a longitudinal section taken along line 9-9 of FIG. 8B.

Referring to FIG. 9, which is schematic of a side view of a longitudinal section taken along line 8-8 of FIG. 8B, anchor engagement element 40 is shown in contact with anchor 10. Engagement feature 41 of engagement element 40 is configured to interact with at least a portion of anchor 10 such that engagement feature 41 is capable of moving anchor 10 distally along elongate member 36 of anchor receiving element 30 when engagement element is moved distally relative to elongate member 36 of anchor receiving element 30. In the embodiment depicted in FIG. 9, and as discussed above with regard to FIGS. 7C, 8E and 8G, engagement feature 41 defines channel 45 and proximal opening 42 of engagement element 40. The opening 42 defined by engagement feature 41, in the depicted embodiments, has dimensions that are smaller than at least a portion of the outer diameter of the body member 11 of the anchor 10.

The anchor deployment tools depicted in FIGS. 7-9 allows for kits having multiple anchor receiving elements 30 with preloaded anchors 10 to be provided with a single anchor engagement element 40. An anchor receiving element 30 may readily be inserted and withdrawn from engagement element 40, allowing for re-insertion of the same or another anchor receiving element 30. However, embodiments where anchor receiving element 30 is not removable and reinsertable into anchor engagement element 40 are envisioned.

Figure 10A:
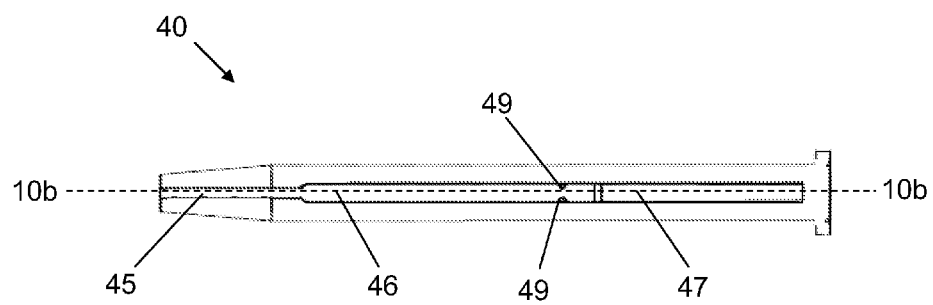
FIG. 10A is a schematic diagram of a side view of an anchor engagement element.

Referring now to FIG. 10A, a schematic drawing of a side view of an embodiment of an anchor engagement element 40 is shown. The engagement element 40 may include one or more stop features 49 protruding into the passageway formed by slot 48 and second channel 46 (see, e.g., FIGS. 7C, 7D and 7F). The stop features 49 are configured and positioned engage a handle 38 of an anchor receiving element 30 (see, e.g., FIGS. 7-9) and, once engaged, to prevent further proximal movement of handle 38 within the opening formed by the slot and second channel of engagement element 40. The engagement element 40 may further include a deflecting element 47 extending in the passageway formed by the slot 48 and second channel 46 and configured to deflect proximal end 24 of therapy delivery element 20 (see, e.g., FIG. 9) in embodiments where therapy delivery element 20 may extend beyond a proximal portion or handle 38 of anchor receiving element 30.

Figure 10B:
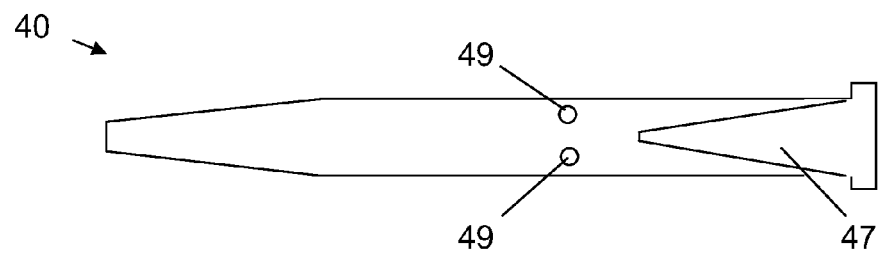
FIG. 10B is a schematic drawing of a top view of a longitudinal section of the anchor engagement element taken at line 10b-10b of FIG. 10A.

Referring to FIG. 10B, in which a schematic drawing of a top view of a longitudinal section taken at line 10b-10b of FIG. 10A is shown, deflecting element 47, in the depicted embodiment, is wedge shaped and is capable of causing deflection of an end portion of a therapy delivery element that is advanced proximally within a lumen of an anchor receiving element that is disposed with the anchor engagement element 40 to deflect out of a side (e.g., slot 48 or channel 46) of the engagement element 40 to prevent backing up of therapy delivery element 20 and to allow for relatively proximal movement of therapy delivery element with in the context of the systems described herein.

Anchor engagement element 40 may be formed from any suitable material. Preferably the body of engagement element 40 is formed from a rigid material, such as stainless steel, titanium, polycarbonate, polypropylene, or the like. In various embodiments, the body of engagement element 40 is formed of a polymer having a durometer of about 75 D or higher. In various embodiments, engagement element 40 is molded in its entirety.

Figure 11:
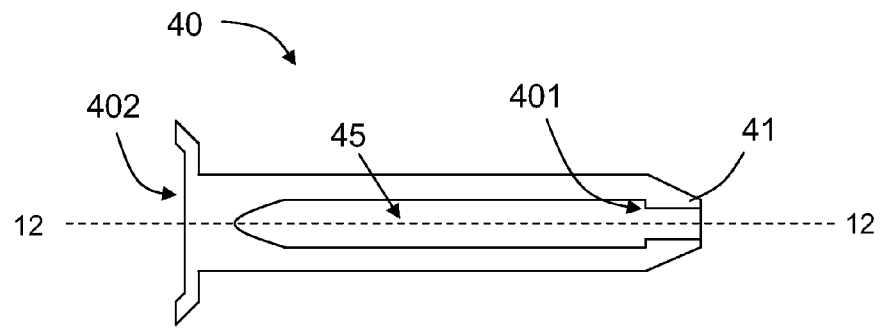
FIG. 11 is a schematic top exploded view of an embodiment of an anchor deployment apparatus.

Referring now to FIG. 11, an alternative embodiment of an anchor deployment apparatus is shown. The apparatus includes an anchor engagement element 40, an anchor receiving element 30, and an alignment element 300 which may be a portion of the anchor receiving element 30 as depicted in FIG. 11. For example, in the depicted embodiment, the alignment element 300 serves as a handle for the anchor receiving element 30. The alignment element 300 is secured relative to the anchor receiving element 30 and facilities alignment of elongate member 36 of the anchor receiving element 30 with the channel 45 of the anchor engagement element 40. The alignment element 300 also includes a rail 31 (depicted within dashed lines in FIG. 11, as the rail projects into the page in the depicted view). The rail 31 is slidably receivable by the channel 45 of the anchor engagement element 40 and serves to facilitate alignment of the elongate member 36 of the anchor receiving element 30 with the channel 45. In some embodiments, the rail 31 and the elongate member 36 are coaxially aligned.

As with the previously presented and described embodiments, the anchor receiving element 30 of the anchor deployment apparatus depicted in FIG. 11 has an elongate member 36 having a proximal opening 32 and a lumen extending distaly in the elongate member from the proximal opening. The lumen of the elongate member is configured to slidably receive at least a portion of a therapy delivery element. The elongate member 36 may also include a distal opening 34, e.g. as depicted, so the lumen extends through the elongate member 36 from the distal opening 32 to the proximal opening 34, allowing the therapy delivery element to be slid through and to extend beyond the lumen of the elongate member 36.

As with the previous embodiments, the anchor engagement element 40 includes an elongate body that forms a channel 45 that extends proximally from the distal end of the element 40. The anchor engagement element 40 includes engagement feature 41 forming at least a part of the channel 45. The feature 41 (in the depicted case, the proximal face of the element 40) is configured to engage an anchor when the anchor is disposed about the elongate member 36 of the anchor receiving element 30 and the elongate member 36 is moved distally relative to the engagement element 41, and to cause the anchor to move distally along the elongate member 36 when the feature 41 is engaged with the anchor and the elongate member 36 is moved distally relative to the engagement element 41. The depicted anchor engagement element 40 also includes a stop feature 410 that protrudes into the channel 45 and is configured and positioned to engage a portion of the alignment element 300 to prevent the alignment element 300 from being moved proximally in the channel 45 once engaged by the stop feature 401. The depicted anchor engagement element 40 also includes a feature 402 for placement of a digit, such as a thumb, to aid in using the apparatus to deploy an anchor (see, e.g., FIG. 8 for general use for deploying an anchor).

In the embodiment depicted in FIG. 11, the alignment element 300 serves as a handle for the anchor receiving element 30. The depicted alignment element 300 includes a proximal portion 310 and a distal portion 320 separated by an indent or gap 33, while the rail 31 extends through the proximal 310 and distal 320 portions. The depicted alignment element 300 also includes laterally extending features 39 for placement of digits, such as a the index and middle fingers, to aid in using the apparatus to deploy an anchor.

Figure 12:
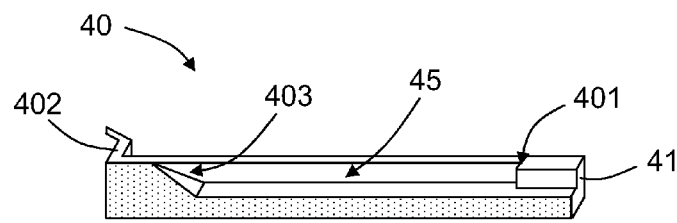
FIG. 12 is a schematic perspective view of an embodiment of an anchor engagement element with a longitudinal section taken through line 12-12 of FIG. 11.

Referring now to FIG. 12, a schematic perspective view of an embodiment of the anchor engagement element 40 depicted in FIG. 11, taken through line 12-12, is shown, with like reference numbers referring to like components or features. As shown in the embodiment depicted in FIG. 12, the channel 45 contains a ramp 403 tapering from the bottom of the channel 45 to the surface of the body of the anchor engagement element 40 at a distal portion of the element. The ramp 403 facilitates exit and extension of a proximal portion of a therapy delivery element beyond a distal portion of the channel when the therapy delivery element is slid proximally in the channel. Thus, the ramp 403 serves a similar function to the deflecting element (47) depicted in FIG. 10.

Figure 13A:
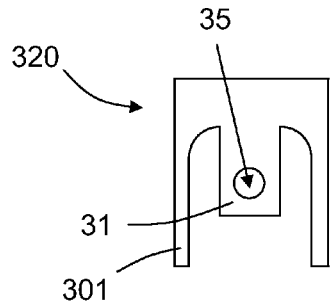
FIGS. 13A-B are schematic sectional views of embodiments of portions of an alignment element with sections taken through lines 13a-13a and 13b-13b of FIG. 11, respectively.
Figure 13B:
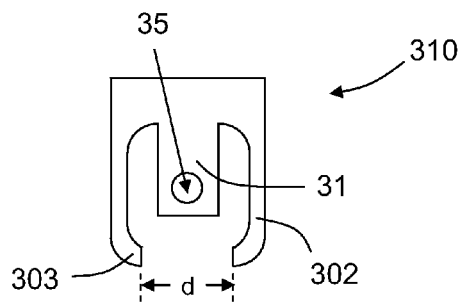

Referring now to FIGS. 13A-B, sectional views of embodiments of the alignment element 300 depicted in FIG. 11, taken through lines 13a-13a and 13b-13b, respectively, are shown. The depiction in FIG. 13A is of a section taken through the distal portion 320 of the alignment element, and the depiction in FIG. 13B is of a section taken through the proximal portion 310 of the alignment element. The rail 31 extends through the proximal 310 and distal 320 portions of the alignment element. In the depicted embodiment, the alignment element and the anchor receiving element are a single element and the lumen 35 of the elongate member extends through the rail 31.

The distal portion 320 of the alignment element in the embodiment depicted in FIG. 13A includes opposing alignment arms 301 that project in the same direction as the rail 31 and are configured to slidably dispose about opposing sides of the anchor engagement element when the anchor deployment tool is assembled and ready for use.

The proximal portion 310 of the alignment element in the embodiment depicted in FIG. 13B includes opposing deflectable alignment arms 302 that project in the same direction as the rail 31 and are configured to slidably dispose about opposing sides of the anchor engagement element when the anchor deployment tool is assembled and ready for use. The deflectable arms 302 include inwardly extending distal portions 303 that are separated by a distance (d) less than a width of at least a portion of the body of the anchor engagement element, which will be discussed in more detail below. The distance (d) is defined in a relaxed state, in which no external forces are placed on the arms 302. The arms 302 are outwardly deflectable such that the inwardly extending portions 303 may be advanced about the body of the anchor engagement element beyond the portion having a width greater than the distance between the inwardly extending portions in a relaxed state.

Figure 14:
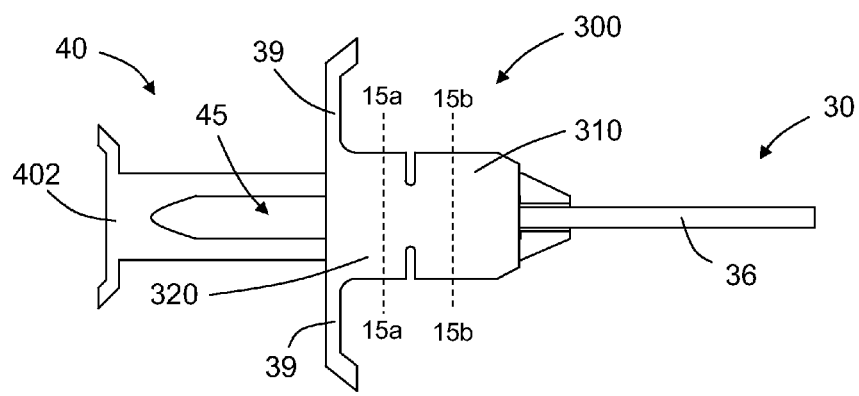
FIG. 14 is a schematic top view of an embodiment of anchor deployment apparatus.
Figure 15A:
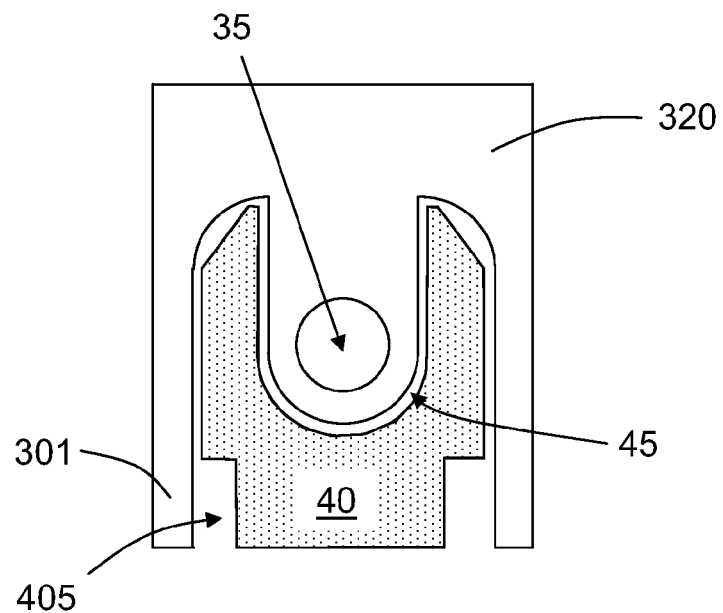
FIGS. 15A-B are schematic sectional views of embodiments of portions of an anchor deployment apparatus with sections taken through lines 15a-15a and 15b-15b of FIG. 14, respectively.
Figure 15B:
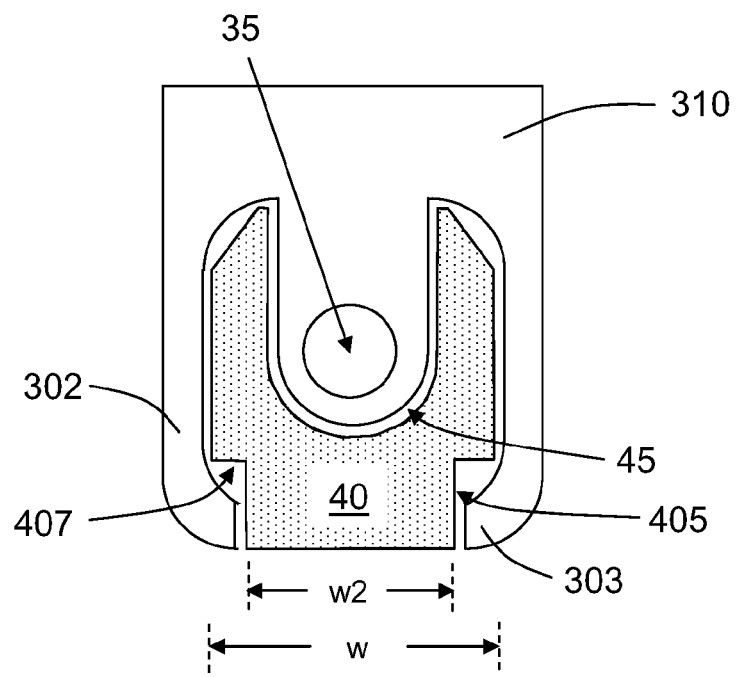

Referring now to FIGS. 14-15, an embodiment of an assembled anchor deployment apparatus is shown in FIG. 14, and sections taken through lines 15a-15a and 15b-15b are shown in FIGS. 15A and 15B, respectively. Like numbers in FIGS. 14-15 and FIGS. 11-13 refer to like components, features, or the like. As shown in FIGS. 15A-B, the rail 31 of the alignment element is shaped in a manner complementary to the channel 45 formed by the body of the anchor engagement element 40B to facilitate sliding of the rail 31 in the channel 45.

The alignment arms 301, 302 are depicted in a relaxed state in FIGS. 15A-B and are disposed about the sides of the body of the anchor engagement element 40. As illustrated in FIG. 15B, the deflectable arms 302 include inwardly extending distal portions 303 that are separated by a distance less than a width (w) of at least a portion of the body of the anchor engagement element The arms 302 are outwardly deflectable such that the inwardly extending portions 303 may be advanced about the body of the anchor engagement element beyond the portion having a width (w) greater than the distance between the inwardly extending portions in a relaxed state. In the depicted embodiment, the body of the anchor engagement element 40 includes generally opposing indented portions 405 (at the bottom of the drawings in FIGS. 15A-B) having a width (W2) about equal to or less than the distance between the inwardly deflectable portions in a relaxed state and are configured to receive the inwardly extending portions of the first and second deflectable arms. The indented portions 405 extend a distance along the length of the body of the anchor receiving element and are configured to slidably receive the inwardly extending portions 303 of the deflectable arms 302. Thus, when the depicted anchor deployment tool is fully assembled and ready for use, the inwardly extending portions 303 are in close proximity to or in contact with the indented portions 405 of the anchor engagement element 40. A shoulder 407 formed by the indented portion 405 inhibits accidental withdrawal of the alignment element from about the engagement element 40 with the inwardly extending elements 303 configured to engage the shoulder 407 to resist such withdrawal, absent sufficient force.

Accordingly, the alignment element snaps or clicks into place about the anchor engagement element 40. Preferably, the alignment element is able to be repeatedly snapped or clicked into place about the engagement element 40 and repeatedly removed from about the engagement element 40.

The tolerances shown in the FIGS. 15A-15B are for purposes of illustration and are not necessarily to scale.

It will be understood that an alignment element need not include both proximal 310 and distal 320 portions or may include more than one proximal or distal portions. Referring back to FIG. 11, a gap 33 is shown separating the proximal 310 and distal 320 portions of the alignment element 300. It will be understood that the distal portion (or equivalent thereof) may be located proximally to the proximal portion (or vice versa). It will be understood that no gap or feature is needed to separate the two portions. It will also understood that the presence of the distal 320 portion of the alignment element facilitates alignment of the element with the channel of the anchor engagement element but does no contribute substantially to the force required to place or withdraw the alignment element about the anchor engagement element. Accordingly, the force required for such placement or withdrawal may be tailored by balancing the relative ratio of the distal 320 to proximal 310 portions.

In some embodiments, the alignment element 300 includes only the proximal portion 310. In some embodiments, the alignment element 300 includes more than one proximal portion 310 or more than one distal portion 310.

Referring now to FIGS. 16A-16B, alternative embodiments of sectional views of proximal 310 and distal 320 portions of the alignment element shown in FIG. 11, taken through lines 12a-12a, respectively, are shown. In the depicted embodiments, the anchor receiving element and the alignment elements are formed from different parts. The elongate member 36 forming the lumen 35 of the anchor receiving element is secured in a lumen formed in the rail 31 of the alignment element.

Of course, the alignment element and the anchor receiving element or components thereof may be formed from one or more parts. Any suitable material may be used for forming the alignment element, the anchor receiving element, or a component thereof. Preferably the alignment element or the anchor receiving element, or suitable portions thereof, are formed from a rigid material, such as stainless steel, titanium, polycarbonate, polypropylene, or the like. In various embodiments, the alignment element, the anchor receiving element, or components thereof are formed of a polymer having a durometer of about 75 D or higher. In various embodiments, alignment element or the anchor receiving element are molded in their entireties.

Figure 19:
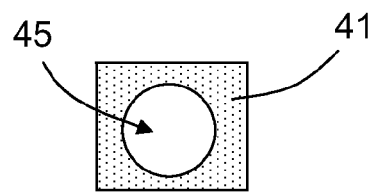
FIG. 19 is a schematic sectional view of an embodiment of the anchor engagement element depicted in FIG. 18, taken through line 19-19.

Referring now to FIGS. 17-18, an embodiment of and anchor deployment tool having an anchor engagement element 40 having an engagement feature 41 that completely surrounds a channel 45 is shown. In FIG. 17 a top view of the fully assembled anchor deployment tool is shown; in FIG. 18 a top view of an anchor engagement element is shown; and in FIG. 19 a sectional view taken through line 19-19 of FIG. 18 is shown. The numerical references shown in FIGS. 17-19 refer to similar references used in FIGS. 11-16. The embodiment of the anchor deployment tool depicted in FIGS. 17-19 provides for more reproducible deployment of an anchor, due to 360 degree contact with the engagement feature 41 that surrounds the channel 45, relative to the embodiments depicted in FIGS. 11-15 in which the engagement feature only partially surrounds the channel.

However, exchange (removal and placement) of the combined alignment element and anchor receiving element from the anchor engagement element is easier with regard to the embodiments depicted in FIGS. 11-15, because the combined alignment element and anchor receiving element can be removed from and placed about the anchor engagement element while the anchor is disposed about the elongate element of the anchor receiving element. However, when the engagement feature (41) surrounds the channel (45), e.g. as in the embodiments depicted in FIGS. 17-19, the anchor needs to be removed from the elongate member of the anchor receiving element prior to removal of the combined alignment element and anchor receiving element from the anchor engagement element.

Figure 20:
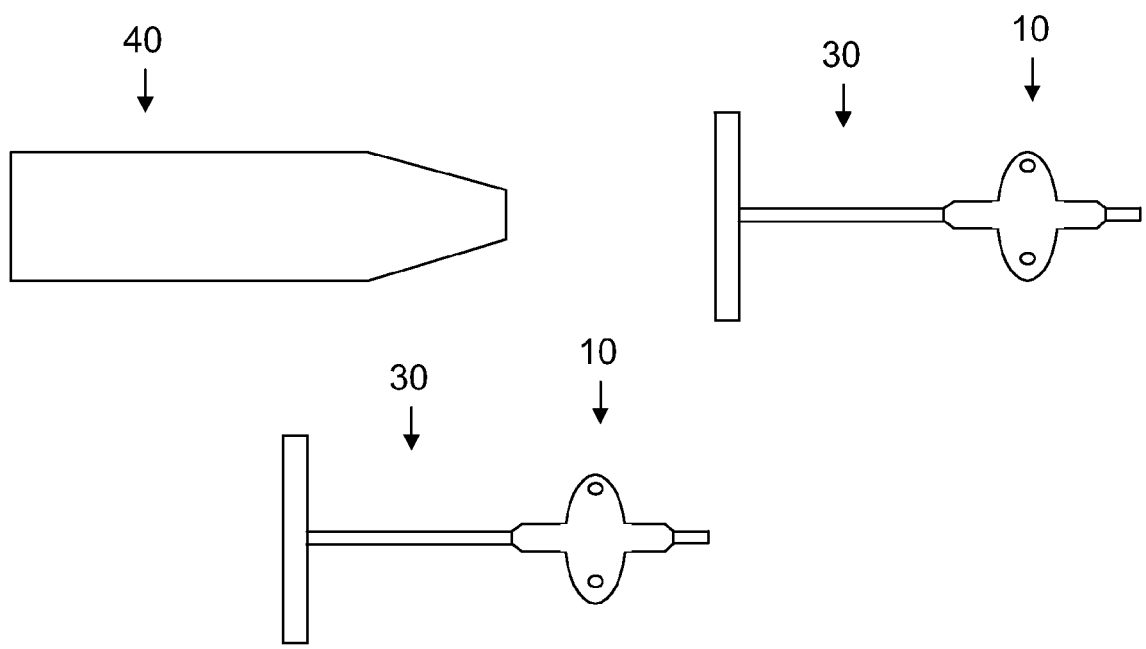
FIG. 20 is a schematic drawing of a top view of components of a kit.

Referring to FIG. 20, a schematic drawing of a top view of representative components of a kit is shown. A kit may include an anchor engagement element 40, an anchor 10, and an anchor receiving element 30. The anchor 30 may be preloaded on the anchor receiving element 30. In various embodiments, a kit includes two or more anchor receiving elements 30 with preloaded anchors 10. In the depicted embodiment, the anchor receiving elements 30 are insertable, removable and reinsertable in the anchor engagement element 40. An anchor receiving element 30 may be preloaded in anchor engagement element 40. A kit may further include a therapy delivery element (not shown in FIG. 20).

Figure 21A:
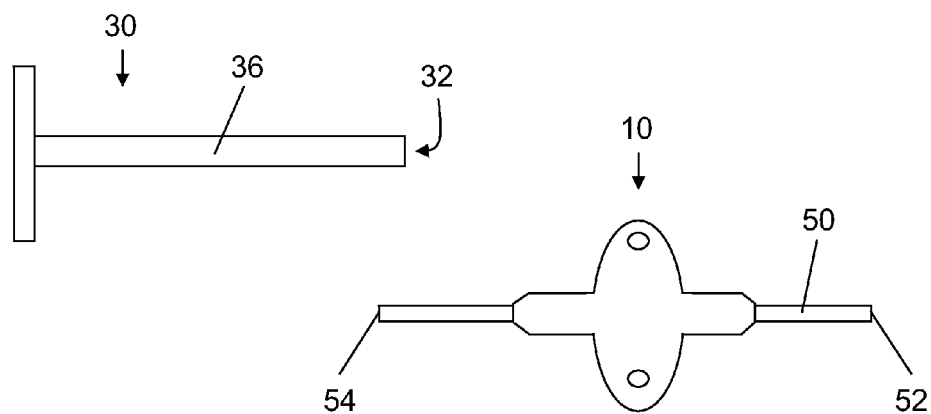
FIGS. 21A-B are schematic drawings of top views of a system including an anchor, an insertion element, and an anchor receiving element.
Figure 21B:
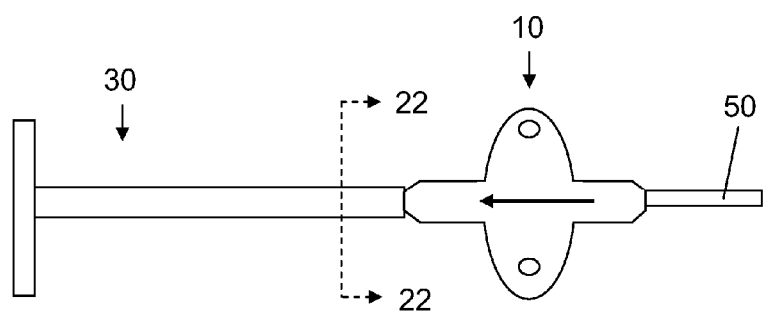
Figure 21C:
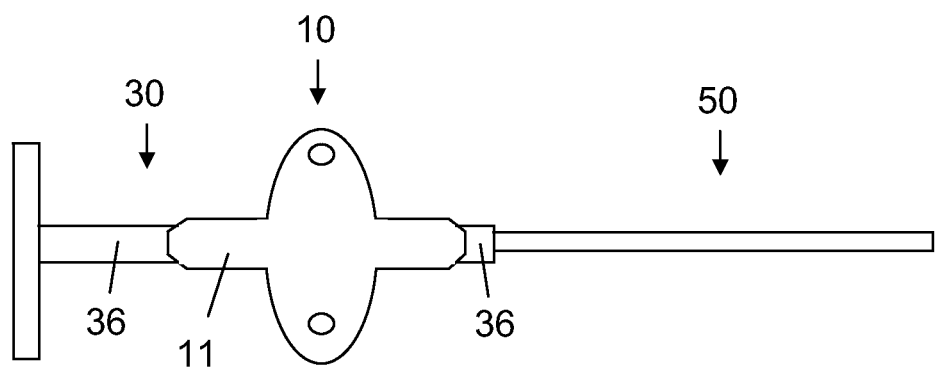
Figure 22:
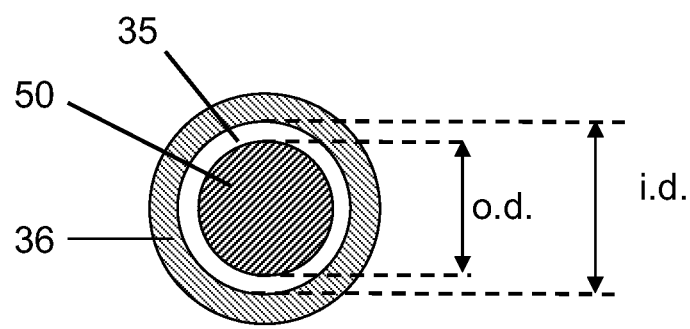
FIG. 22 is a cross section of an anchor diposed about an insertion element taken along line 22-22 of FIG. 21.

Anchor 10 may be loaded on anchor receiving element 30 in any manner that retains the elastic and therapy delivery element-retaining properties of the anchor. One suitable manner for placing anchor 10 about anchor receiving element 30 is shown in FIGS. 21A-C. As shown in FIG. 21A, anchor 10 may be placed about an insertion element 50 having proximal 54 and distal 52 ends. A handle (not shown) may be attached to or form a part of a distal portion of insertion element 50. Proximal end 54 of insertion element 50 may be inserted into a lumen of anchor receiving element 30 via distal opening 32 (see FIG. 21B), and anchor 10 may be moved proximally along insertion element 50 and about receiving element 30 until anchor 10 is entirely disposed about elongate member 36 of receiving element 30 (FIG. 11C). As shown in FIG. 22, which is schematic cross section taken through line 12-12 of FIG. 21B, insertion element 50 has an outer diameter (o.d.). The outer diameter (o.d.) is larger than the relaxed inner diameter of anchor body 11 and smaller than a radially stretched inner diameter of anchor body 11 (see FIG. 3B). The outer diameter (o.d.) of insertion element 50 is sized to cause some radial expansion of anchor body 11 when anchor 10 is disposed about insertion element 50, but preferably not too much to prevent sliding of anchor 10 about insertion element 50. Insertion element 50 outer diameter (o.d.) is preferably only slightly smaller than the inner diameter (i.d.) of elongate body 36 of receiving member 30 so that when anchor 10 is transferred, via sliding, from insertion element 50 to receiving element 30, lumen 15 extending through anchor body 11 (see FIG. 3B) does not undergo substantial radial expansion, as substantial radial expansion of anchor body 11 may make it difficult to transfer anchor 10 due to the elastic properties of anchor body 11.

Figure 23A:
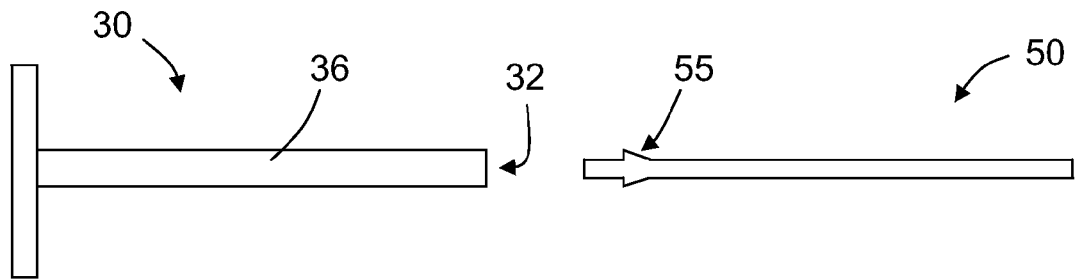
FIG. 23A-B are schematic drawings of top views of alternative embodiments of insertion elements and anchor receiving elements.
Figure 23B:
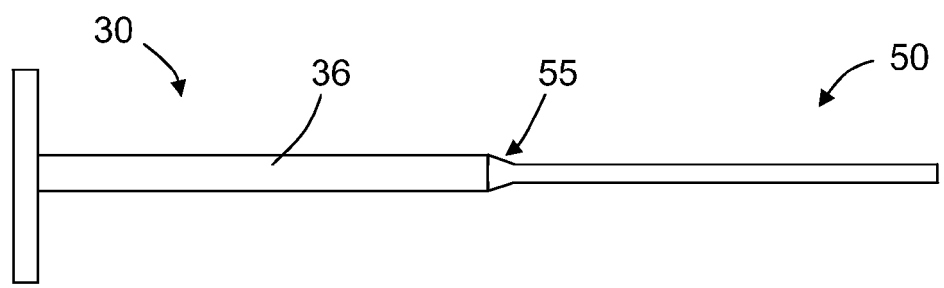
Figure 24A:
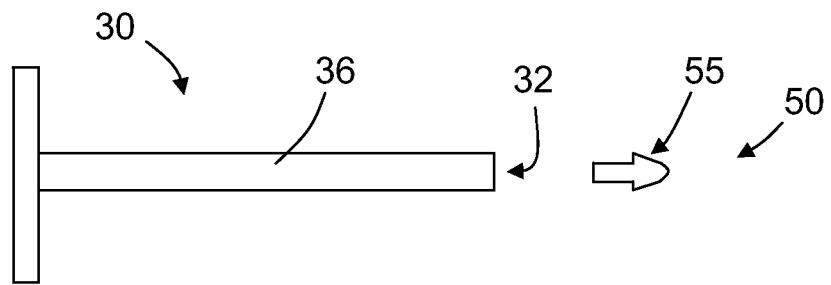
FIG. 24A-B are schematic drawings of top views of alternative embodiments of insertion elements and anchor receiving element.
Figure 24B:
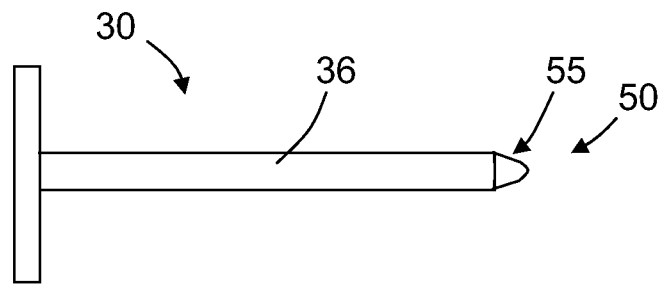

Alternative embodiments of insertions elements are depicted in FIGS. 23-24. As shown in FIG. 23, the insertion element has a cone-shaped feature 55 having a largest outer diameter that is approximately the same as the outer diameter of the elongate member 36. A proximal portion of the insertion element may be inserted into the lumen of the elongate member 36 via opening 32 until the con-shaped feature 55 butts up against the proximal end of the elongate member 36. An anchor may be slid proximally along the insertion element 50 over the cone-shaped member 55 and about the elongate member 36. As shown in FIG. 24, the insertion element 50 need not have a distally extending elongate member. In the embodiment depicted in FIG. 24, the anchor may be manually (or otherwise) fed over the cone shaped feature 55 and onto the elongate member 36. Solvents that swell or facilitate stretching of the anchor may be employed to facilitate the process of loading the anchor on the elongate element. For example, if the anchor is formed of silicone, the anchor may be contacted with, e.g. immersed in, heptane prior to loading.

Insertion element 50 is preferably formed from a rigid material, such as stainless steel, titanium, polycarbonate, polypropylene, or the like. In various embodiments, insertion element 50 is formed of a polymer material having a durometer of about 75 D or higher.

Thus, embodiments of ANCHOR DEPLOYMENT APPARATUS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An anchor deployment apparatus for deploying an anchor about a therapy delivery element, comprising:
an anchor receiving element having an elongate member having a distal opening and a lumen extending proximally in the elongate member from the distal opening, the lumen of the elongate member being configured to slidably receive at least a portion of a therapy delivery element;
an anchor engagement element having (i) a body forming a channel in which the elongate member of the anchor receiving element is axially movable, and (ii) an engagement feature forming at least a part of the channel,
wherein the engagement feature is configured to engage the anchor when the anchor is disposed about the elongate member, and to cause the anchor to move distally along the elongate member when the feature is engaged with the anchor and the elongate member is moved proximally relative to the engagement element; and
an alignment element secured relative to the elongate member and configured to secure the elongate member relative to the body of the anchor engagement element to restrict movement of the elongate member orthogonal to the axis of the channel,
wherein the anchor receiving element and the alignment element are formed from the same or different parts.

2. The anchor deployment apparatus of claim 1, wherein the elongate member of the anchor receiving element further comprises a proximal opening and the lumen extends through the elongate member from the proximal opening to the distal opening.

3. The anchor deployment apparatus of claim 1, wherein the alignment element comprises first and second opposing deflectable arms, wherein in a relaxed configuration at least a portion of the deflectable arms on are separated by a distance less than a width of at least a portion of the body of the anchor engagement element.

4. The anchor deployment apparatus of claim 3, wherein the first and second deflectable arms comprise inwardly extending portions separated by the distance less than a width of at least a portion of the body of the anchor engagement element, wherein the first and second arms are outwardly deflectable such that the inwardly extending portions may be advanced about the body of the anchor engagement element beyond the portion having a width greater than the distance between the inwardly extending portions in a relaxed state.

5. The anchor deployment apparatus of claim 4, wherein the body of the anchor engagement element comprises an first and second generally opposing indented portions having a width less than the distance between the inwardly deflectable portions in a relaxed state and are configured to receive the inwardly extending portions of the first and second deflectable arms.

6. The anchor deployment apparatus of claim 5, wherein the indented portions extend a distance along the length of the body of the anchor receiving element and are configured to slidably receive the inwardly extending portions of the first and second deflectable arms.

7. The anchor deployment apparatus of claim 1, wherein the alignment element further comprises a rail slidably receivable by the channel of the anchor engagement element.

8. The anchor deployment apparatus of claim 7, wherein the rail is coaxial with the elongate member of the anchor receiving element.

9. The anchor deployment apparatus of claim 1, wherein the alignment element forms a part of a handle of the anchor receiving element.

10. The anchor deployment apparatus of claim 1, wherein the anchor engagement element further comprises a stop feature that protrudes into the channel, wherein the stop feature is configured and positioned to engage the alignment element and to prevent the alignment element from being moved proximally in the channel once engaged by the stop feature.

11. The anchor deployment apparatus of claim 1, wherein the anchor engagement feature completely surrounds a portion of the channel.

12. The anchor deployment apparatus of claim 1, wherein the channel comprises a distal ramp to facilitate exit and extension of a proximal portion of a therapy delivery element beyond a distal portion of the channel when the therapy delivery element is slid proximally in the channel.

13. A system comprising:
- an anchor having a first opening, a second opening, a body member disposed between the first and second opening, and a lumen extending though the body member from the first opening to the second opening, wherein the body member is formed from an elastic material and wherein at least a portion of the body member has a first inner diameter defined by the lumen in a relaxed state and a second inner diameter defined by the lumen in a radially stretched state, wherein the first inner diameter is smaller than the second inner diameter;
- a therapy delivery element having an outer diameter and an outer surface about which the anchor is disposable, the outer diameter being larger than the first inner diameter of the at least a portion of the lumen of the anchor and smaller than the second inner diameter of the at least a portion of the lumen of the anchor; and
- an anchor deployment apparatus according to claim 1.

14. A kit comprising:
- an anchor having (i) a first opening, (ii) a second opening, (iii) a body member disposed between the first and second opening, (iv) a lumen extending though the body member from the first opening to the second opening, and (v) a retention element secured to or integrally formed with the body member,
    - wherein the body member is formed from elastic material, the lumen is configured to be disposed about at least a portion of the outer surface of a therapy delivery element, and at least a portion of the body member has a first inner diameter defined by the lumen in a relaxed state and a second inner diameter defined by the lumen in a radially stretched state, the first inner diameter being smaller than the second inner diameter; and
- and an anchor deployment apparatus according to claim 1,
    - wherein the elongate member of the anchor receiving element of the anchor deployment apparatus has an outer diameter larger than the first inner diameter of the at least a portion of the lumen of the anchor and smaller than the second inner diameter of the at least a portion of the lumen of the anchor such that the anchor is disposable about the elongate member and, when the anchor is disposed about the elongate member, the at least a portion of the lumen of the anchor engages at least a portion of the elongate member, and wherein the anchor is moveable about the elongate member.

15. The kit according of claim 14, wherein the anchor is preloaded about the elongate member of the anchor receiving element.

16. The kit of claim 15, wherein the kit comprises more than one anchor receiving elements, wherein an anchor is preloaded about each of the elongate members of the anchor receiving elements.

17. The kit of claim 16, wherein each preloaded anchor is different.

18. The kit of claim 14, wherein the body member of the anchor is formed from silicone.

19. The kit of claim 14, further comprising the therapy delivery element.

20. The kit of claim 19, wherein the therapy delivery element is selected from the group consisting of a lead and a catheter.

\* \* \* \* \*

UNITED STATES PATENT AND TRADEMARK OFFICE
CERTIFICATE OF CORRECTION

| | | |
|---|---|---|
| PATENT NO. | : 8,632,502 B2 | Page 1 of 1 |
| APPLICATION NO. | : 12/896147 | |
| DATED | : January 21, 2014 | |
| INVENTOR(S) | : Bruce Behymer et al. | |

It is certified that error appears in the above-identified patent and that said Letters Patent is hereby corrected as shown below:

In the Claims

<u>Column 16, line 31, Claim 3</u>: "arms on are separated by a" should correctly read -- arms are separated by a --.

<u>Column 16, lines 44-45, Claim 5</u>: "comprises an first and second generally" should correctly read -- comprises a first and second generally --.

<u>Column 18, line 21, Claim 15</u>: "The kit according of claim" should correctly read -- The kit according to --.

Signed and Sealed this
Fourteenth Day of July, 2015

Michelle K. Lee
*Director of the United States Patent and Trademark Office*